US00PP26563P2

(12) United States Plant Patent
Egger

(10) Patent No.: US PP26,563 P2
(45) Date of Patent: Mar. 29, 2016

(54) ***AGASTACHE* PLANT NAMED 'KUDOS YELLOW'**

(50) Latin Name: ***Agastache* hybrid**
Varietal Denomination: Kudos Yellow

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/544,492

(22) Filed: Jan. 13, 2015

(51) Int. Cl.
*A01H 5/02* (2006.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct form of *Agastache* plant characterized by numerous yellow flowers on long, dense inflorescences, a long bloom time, a short, compact habit, good winter hardiness, and excellent vigor.

1 Drawing Sheet

Botanical denomination: *Agastache* hybrid.
Variety designation: 'Kudos Yellow'.

BACKGROUND OF THE INVENTION

The present invention relates to a new and distinct cultivar of *Agastache*, given the name, 'Kudos Yellow'. *Agastache* is in the family Lamiaceae. This new variety is one of several selections of new *Agastache* using hardy and dwarf *Agastache* species in the breeding lines to provide hardiness and compactness. The new cultivar is a selection from the cross between *Agastache* AO-var, as the seed parent, and *Agastache* 207-5, as the pollen parent. The new cultivar was selected for its compact habit, hardiness, and masses of yellow flowers in dense heads.

Compared to the seed parent, *Agastache* AO-var, the new cultivar has yellow flowers rather than yellow orange.

Compared to the pollen parent, *Agastache* 207-5, the new cultivar has yellow flowers rather than light yellow orange.

Compared to *Agastache* 'Kudos Gold', U.S. Plant patent application No. 14/120,308, the new cultivar is similar except for the flower color which is yellow rather than light yellow orange.

Compared to *Agastache aurantiaca* 'Sunset Yellow', an unpatented plant, the new cultivar has much larger and denser inflorescences and a bushier more upright habit.

Compared to *Agastache mexicana* Acapulco® 'White & Yellow', an unpatented plant, the new cultivar has much larger and denser inflorescences and a bushier more upright habit. The flower color of the new cultivar is more yellow.

This plant exhibits the following characteristics that make it unique:

1. numerous yellow flowers on long, dense inflorescences,
2. a long bloom time,
3. a short, compact habit,
4. good winter hardiness, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a side view of a six-month-old *Agastache* 'Kudos Yellow' plant of the new cultivar grown in a one gallon container in July in Canby, Oreg.

FIG. 2 shows one-year-old *Agastache* 'Kudos Yellow' growing in the field in mid summer in Canby, Oreg.

DETAILED PLANT DESCRIPTION

The following is a detailed description of the new *Agastache* cultivar based on observations of 6-month-old specimens in July growing in full sun in the field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition, 2007.

Plant:

*Form*.—Upright, bushy, well-branched.
*Type*.—Herbaceous perennial.
*Cold hardiness*.—USDA Zone 6-10.
*Size*.—Grows to 52 cm wide and 50 cm tall to the top of the flowers.
*Vigor*.—Excellent.
*Branching*.—About 12 main stems from the base, these branch at every node.

*Stem*.—Square in cross section, grows to 4 mm wide and 27 cm tall to the first flower, pubescent, internodes range from 2 cm to 5 cm long, Yellow Green 146B.

*Roots*.—White 155B, fibrous, plants root easily from stem tip cuttings.

Leaf:

*Type*.—Simple.

*Arrangement*.—Opposite.

*Shape*.—Ovate to triangular.

*Venation*.—Pinnate.

*Margins*.—Crenate.

*Apex*.—Acute.

*Base*.—Truncate.

*Blade size*.—Grows to 40 mm long and 25 mm wide.

*Surface texture*.—Pubescent on both sides.

*Petiole description*.—Grows to 12 mm long and 1 mm wide, pubescent, Yellow Green 147B.

*Leaf color*.—Top side Green 137A with vein 147B, bottom side closest to Yellow Green 147B with vein 147C.

*Fragrance*.—Aromatic.

Inflorescence:

*Type*.—Terminal spike with up to 14 whorls.

*Number of flowers*.—About 300 per spike.

*Size of inflorescence*.—Grows to 20 cm tall and 5 cm wide.

*Peduncle*.—Grows to 7 cm tall and 2 mm wide, pubescent, Yellow Green 147B.

*Pedicel*.—Grows to 2 mm long, pubescent, Yellow Green 147C.

*Bloom period*.—June through frost in Canby, Oreg.

Flower bud:

*Size*.—20 mm long and 4 mm wide at the widest point prior to opening.

*Description*.—Tubular.

*Surface texture*.—Pubescent.

*Color*.—Yellow Orange 15C.

Flower:

*Type*.—Zygomorphic.

*Shape*.—Bilabiate, tubular.

*Size*.—25 mm long and 5 mm wide.

*Corolla description*.—25 mm long and 5 mm wide; overall color both sides Yellow 13A, old flowers may turn Orange Red 35C on tube before senescing; glabrous inside and pubescent outside, tube 20 mm long and 1 mm to 4 mm wide; 2 upper lobes joined 4 mm long and 3 mm wide, each oblong, tips acute, margin entire; three lower lobes, two spreading sideways, ovate, each 3 mm long and 3 mm wide, tip acute, margin entire; bottom lobe cupped, broadly obovate, notched at the tip, margin entire to occasionally serrate, 5 mm wide and 4 mm deep.

*Calyx description*.—Campanulate, 7 mm long and 2.5 mm wide, pubescent outside and glabrous inside, 5 lobed, lobes lanceolate, 2.5 mm long, margins entire, tips acuminate, Yellow Green 147C inside and outside, lobe edges tinted with Greyed Orange 177A.

*Pistil description*.—One, exerted, 21 mm long, ovary 1 mm long, Yellow Green 145C, style 19 mm long, White NN155C, stigma two-parted, 1 mm deep, Greyed Purple 186C.

*Stamen description*.—4 in number, paired, top two 20 mm long and bottom two 17 mm long, filaments White NN155C, anthers 0.4 mm long, Greyed Orange 178A, pollen none.

*Fragrance*.—Aromatic.

*Lastingness*.—A spike blooms for about 4 weeks on the plant.

Fruit/seed: 4 nutlets, 1 mm long, ovoid, Black 202A, very low fertility.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

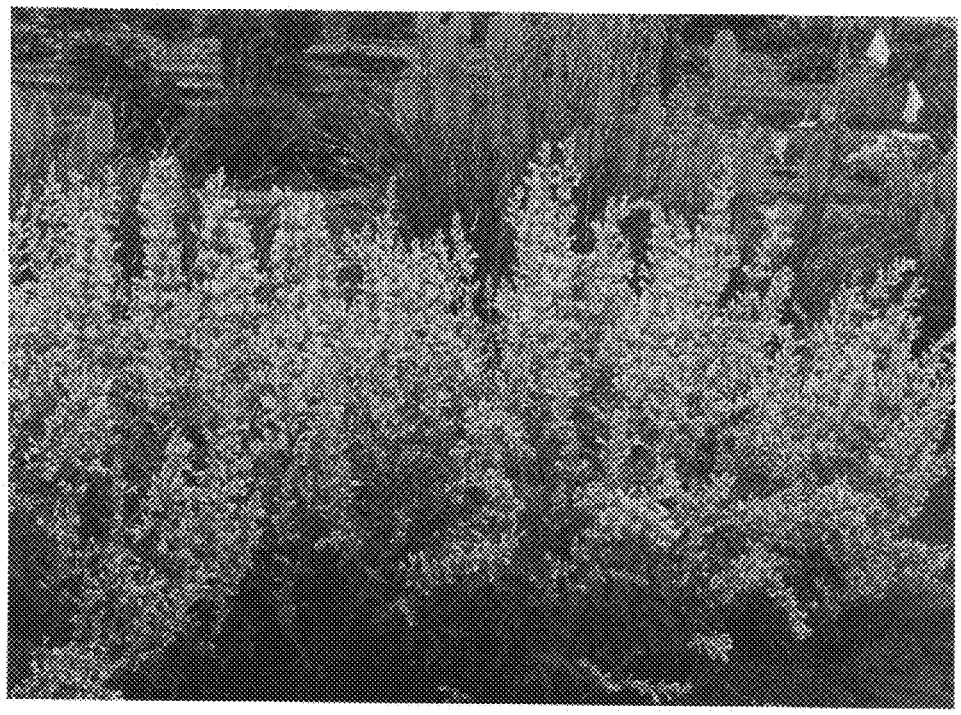

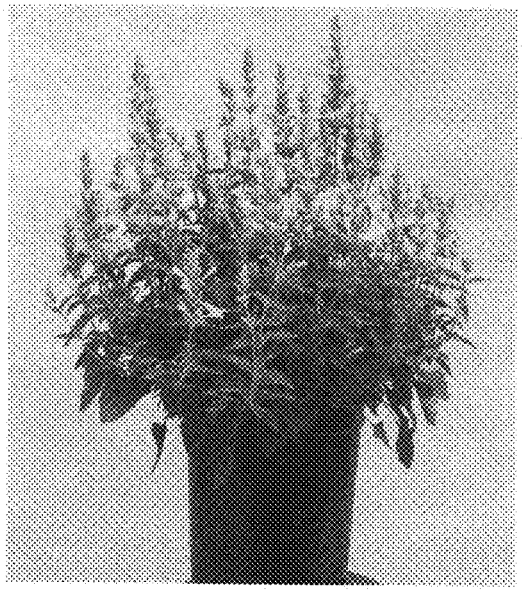
FIG. 1 on left
FIG. 2 below